(12) United States Patent
Timberlake et al.

(10) Patent No.: US 8,158,038 B2
(45) Date of Patent: Apr. 17, 2012

(54) FLAME RETARDANT HALOGENATED POLYMER COMPOSITIONS

(75) Inventors: Larry D. Timberlake, West Lafayette, IN (US); James D. Siebecker, West Lafayette, IN (US)

(73) Assignee: Chemtura Corporation, Middlebury, CT (US)

( * ) Notice: Subject to any disclaimer, the term of this patent is extended or adjusted under 35 U.S.C. 154(b) by 0 days.

(21) Appl. No.: 12/909,923

(22) Filed: Oct. 22, 2010

(65) Prior Publication Data

US 2011/0040003 A1    Feb. 17, 2011

Related U.S. Application Data

(63) Continuation of application No. 12/148,188, filed on Apr. 16, 2008, now abandoned.

(60) Provisional application No. 60/926,374, filed on Apr. 25, 2007.

(51) Int. Cl.
*C09K 21/00* (2006.01)

(52) U.S. Cl. ........ 252/609; 525/132; 525/133; 525/420; 525/437; 525/471; 524/371; 528/212

(58) Field of Classification Search .................. 252/609; 525/132, 133, 420, 437, 471, 534; 524/371; 528/212

See application file for complete search history.

(56) References Cited

U.S. PATENT DOCUMENTS

| 3,760,003 | A | 9/1973 | Asadorian et al. |
| 3,929,901 | A | 12/1975 | Darsow et al. |
| 4,141,880 | A | 2/1979 | Nametz et al. |
| 4,258,175 | A | 3/1981 | Chen |
| 4,287,373 | A | 9/1981 | Garman et al. |
| 5,530,044 | A | 6/1996 | Mack et al. |

FOREIGN PATENT DOCUMENTS

| EP | 0 018 632 A1 | 11/1980 |
| EP | 1 160 627 A1 | 12/2001 |
| EP | 1 288 191 A | 3/2003 |
| GB | 1182226 | 2/1970 |
| GB | 1265443 | 3/1972 |
| JP | 02 129137 | 5/1990 |

OTHER PUBLICATIONS

De Pasquale et al. "*Further Studies on Reactions of Perfluorophenolates with Substituted Pentafluorobenzens and Perfluorocyclohexane*" The Journal of Organic Chemistry. vol. 33, No. 2 (1968) pp. 830-833.

Laskoski et al. "*Oligomeric Cyanate Ester Resins: Application of a Modified Ullman Synthesis in the Preparation of Thermosetting Polymers*" Journal of Polymer Science. Part A: Polymer Chemistry. vol. 44, pp. 4559-4565 (2006).

Denivelle et al. *Sue l'oxydation de Phenols Benzeniques Pentahalogenes.* C.R. Acad.Sc. Paris. Serie C. vol. 272 (1971) pp. 653-656.

Dhanesar et al. *Synthesis and Stationary Phase Properties of Bromophenyl Ethers* Journal of Chromatography. 267 (1983) pp. 293-301.

*Primary Examiner* — Randy Gulakowski
*Assistant Examiner* — Shane Fang
(74) *Attorney, Agent, or Firm* — Joseph Suhadolnik

(57) ABSTRACT

A halogenated aryl ether oligomer is formed by halogenation of an aryl ether oligomer and is useful as a flame retardant for flammable macromolecular materials. Typically, the halogenated aryl ether oligomer comprises the following repeating monomeric units:

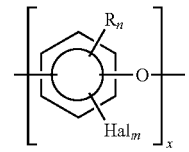

wherein R is hydrogen or alkyl, especially $C_1$ to $C_4$ alkyl, Hal is halogen, m is at least 1, n is 0 to 3 and x is at least 2.

10 Claims, No Drawings

FLAME RETARDANT HALOGENATED POLYMER COMPOSITIONS

CROSS REFERENCE TO RELATED APPLICATIONS

This application is a continuation of U.S. application Ser. No. 12/148,188, filed Apr. 16, 2008 now abandoned, which claims the benefit of the filing date of U.S. Provisional Application No. 60/926,374 filed Apr. 25, 2007, the entire contents of each being incorporated herein by reference.

FIELD

This invention relates to flame retardant halogenated polymer compositions.

BACKGROUND

Decabromodiphenyl oxide (deca) and decabromodiphenylethane (deca-DPE) are commercially available materials widely used to flame retard various polymer resin systems. The structure of these materials is as follows:

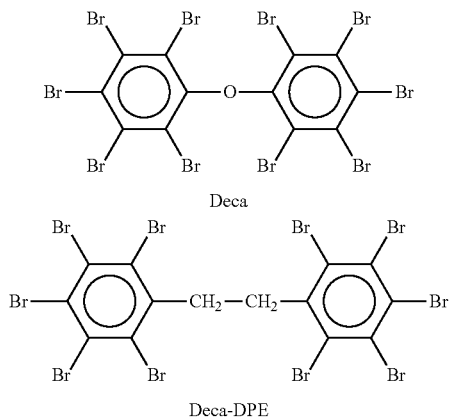

One of the advantages of using deca and deca-DPE in polymer resins that are difficult to flame retard, such as high-impact polystyrene (HIPS) and polyolefins, is that the materials have a very high (82-83%) bromine content. This allows a lower load level in the overall formulation, which in turn serves to minimize any negative effects of the flame retardant on the mechanical properties of the polymer.

Despite the commercial success of deca, there remains significant interest in developing alternative halogenated flame retardant materials that are equally or more efficient, not only because of economic pressures but also because they may allow lower flame retardant loadings, which in turn may impart improved performance properties. Improved properties, such as non-blooming formulations, or better mechanical properties can potentially be met by producing polymeric or oligomeric flame retardant compounds. These types of materials would become entangled in the base resin polymer matrix, depending on the compatibility, and hence should show fewer tendencies to bloom.

There are a number of commercially available flame retardant materials that can be considered oligomers or polymers of halogenated monomers. Examples of these monomers include tetrabromobisphenol A (TBBPA) and dibromostyrene (DBS), which have the following structures:

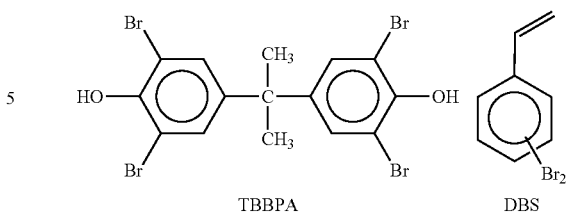

Commercially, TBBPA and DBS are typically not used in their monomeric form, but are converted into an oligomeric or polymeric species. One class of oligomers is the brominated carbonate oligomers based on TBBPA. These are commercially available from Chemtura Corporation (examples include Great Lakes BC-52™, Great Lakes BC-52HP™, and Great Lakes BC-58™) and by Teijin Chemical (FireGuard 7500 and FireGuard 8500). These products are used primarily as flame retardants for polycarbonate and polyesters.

Brominated epoxy oligomers, based on condensation of TBBPA and epichlorohydrin, are commercially available and sold by Dainippon Ink and Chemicals under the Epiclon® series, and also by ICL Industrial Products (examples are F-2016 and F-2100) and other suppliers. The brominated epoxy oligomers find use as flame retardants for various thermoplastics both alone and in blends with other flame retardants.

Another class of brominated polymeric flame retardants based on TBBPA is exemplified by Teijin FG-3000, a copolymer of TBBPA and 1,2-dibromoethane. This aralkyl ether finds use in ABS and other styrenic polymers. Alternative end-groups, such as aryl or methoxy, on this polymer are also known as exemplified by materials described in U.S. Pat. Nos. 4,258,175 and 5,530,044. The non-reactive end-groups are claimed to improve the thermal stability of the flame retardant.

TBBPA is also converted into many other different types of epoxy resin copolymer oligomers by chain-extension reactions with other difunctional epoxy resin compounds, for example, by reaction with the diglycidylether of bisphenol A. Typical examples of these types of epoxy resin products are D.E.R.™ 539 by the Dow Chemical Company, or Epon™ 828 by Hexion Corporation. These products are used mainly in the manufacture of printed circuit boards.

DBS is made for captive use by Chemtura Corporation and is sold as several different polymeric species (Great Lakes PDBS-80™, Great Lakes PBS-64HW™ and Firemaster CP44-HF™) to make poly(bromostyrene) type flame retardants. These materials represent homopolymers or copolymers. Additionally, similar brominated polystyrene type flame retardants are commercially available from Albemarle Chemical Corporation (Saytex® HP-3010, Saytex® HP-7010, and PyroChek 68PB). All these polymeric products are used to flame retard thermoplastics such as polyamides and polyesters.

Unfortunately, one of the key drawbacks of the existing brominated polymer materials is their relatively low bromine content, which makes them less efficient as a flame retardant and consequently typically has a negative effect on the desirable physical properties of the flame retardant formulations containing them, such as impact strength. For example, whereas deca and deca-DPE contain 82-83% bromine, oligomers or polymers based on the brominated monomers mentioned above generally have a bromine content in the range of 52%-68%, depending on the material. This therefore typically requires a flame retardant loading level in a polymer formulation significantly higher than that required for deca, often resulting in inferior mechanical properties for the formulation.

Other considerations also influence the impact the flame retardant has on the final properties of the formulated resin. These considerations include the flame retardant thermal stability and the compatibility with the host resin. In situations where these other considerations are relatively constant, the bromine content, and hence flame retardant load level, has a major influence on the properties of the overall formulation.

To address the need for flame retardant materials that to not detract from the mechanical properties of the target resin, we have now developed a family of materials that can be classified as halogenated, and particularly brominated, aryl ether oligomers. In particular, we have found that the use of these halogenated aryl ether oligomers results in superior mechanical properties in resins such as HIPS and polyolefins and that the materials also provide excellent properties in engineering thermoplastics such as polyamides and polyesters. The aryl ether oligomers can be halogenated to a higher level than the oligomers and polymers that are commercially available today, which should have a positive effect on their mechanical property performance. It is also found that these aryl aryl ether oligomers, even at lower levels of halogenation, give formulations with acceptable mechanical properties Japanese Unexamined Patent Application Publication 2-129,137 discloses flame retardant polymer compositions in which the polymer is compounded a with halogenated bis(4-phenoxyphenyl)ether shown by general formula [I]:

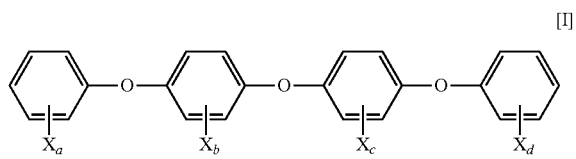

in which X is a halogen atom, a and d are numbers in the range of 1-5, and b and c are numbers in the range of 1-4. However, the flame retardant is produced by brominating the bis(4-phenoxyphenyl)ether as a discrete compound and not an oligomeric material obtained by polymerizing an aryl ether monomer. In contrast, employing a material having an oligomeric distribution as in the present invention is believed to improve its performance properties as a flame retardant.

In an article entitled "Synthesis and Stationary Phase Properties of Bromo Phenyl Ethers, *Journal of Chromatography*, 267 (1983), pages 293-301, Dhanesar et al disclose a process for the site-specific bromination of phenyl ethers containing from 2 to 7 benzene rings. Again the ethers appear to be discrete compounds with no oligomeric distribution and although the products are said to be useful in the separation of organic compounds, no reference is given to their possible use as flame retardants.

SUMMARY

In one aspect, the present invention resides in a halogenated aryl ether oligomer formed by halogenation of an aryl ether oligomer.

Conveniently, the halogen content of the halogenated aryl ether oligomer is in the range of about 50 to about 83 wt %, such as in the range of about 65 to about 80 wt % of the oligomer. Generally, the halogen comprises bromine.

Conveniently, the halogenated aryl ether oligomer has an average of least 3 aryl and typically at least 5 aryl rings. Generally, the molecular weight of the halogenated oligomer is up to 1,000,000 Daltons.

In one embodiment, the halogenated aryl ether oligomer comprises the following repeating monomeric units:

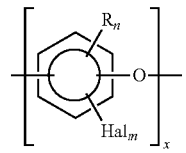

wherein R is hydrogen or alkyl, especially $C_1$ to $C_4$ alkyl, Hal is halogen, normally bromine, m is at least 1, n is 0 to 3 and x is at least 2, such as 3 to 100,000, for example 5 to 20.

In a further aspect, the present invention resides in a flame retardant polymer composition comprising (a) a flammable macromolecular material and (b) a halogenated aryl ether oligomer flame retardant formed by halogenation of an aryl ether oligomer.

In yet a further aspect, the present invention resides in a flame retardant polymer composition comprising (a) a flammable macromolecular material and (b) a halogenated aryl ether oligomer flame retardant formed by halogenation of an aryl ether oligomer wherein said halogenated aryl ether oligomer comprises the following repeating monomeric units:

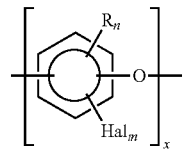

wherein R is hydrogen or alkyl, especially $C_1$ to $C_4$ alkyl, Hal is halogen, normally bromine, m is at least 1, n is 0 to 3 and x is at least 2, such as 3 to 100,000, for example 5 to 20.

Conveniently, said halogenated aryl ether oligomer also comprises end groups each independently comprising an alkyl, alkoxy, aryl, aryloxy, hydrogen, halogen or hydroxyl group.

In still yet a further aspect, the present invention resides in a flame retardant polymer composition comprising (a) a flammable macromolecular material and (b) a halogenated aryl ether flame retardant having the following formula:

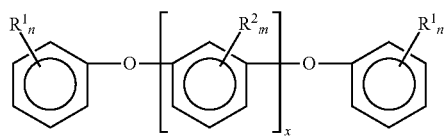

wherein each $R^1$ is independently selected from hydrogen, hydroxy, halogen and alkyl, wherein each $R^2$ is independently selected from hydrogen, hydroxy, halogen and alkyl, provided at least one $R^2$ and normally at least one $R^1$ is halogen, normally bromine, n is 5, m is 4, and x is from 1 to 10, for example from 2 to 6.

Conveniently, the flammable macromolecular material (a) is a thermoplastic polymer, such as polystyrene, poly(acrylonitrile butadiene styrene), a polycarbonate, a polyolefin, a polyester and/or a polyamides.

In one embodiment, the flammable macromolecular material (a) is polystyrene and the amount of halogenated aryl ether oligomer flame retardant in the composition is between about 5 and 25 wt %, such as between about 40 and 20 wt %.

In another embodiment, the flammable macromolecular material (a) is polypropylene and the amount of halogenated aryl ether oligomer flame retardant in the composition is between about 20 and 50 wt %, such as between about 25 and 40 wt %.

In a further embodiment, the flammable macromolecular material (a) is polyethylene and the amount of halogenated aryl ether oligomer flame retardant in the composition is between about 5 and 35 wt %, such as between about 20 and 30 wt %.

In a further embodiment, the flammable macromolecular material (a) is a polyamide or a polyester and the amount of halogenated aryl ether oligomer flame retardant in the composition is between about 5 and 25 wt %, such as between about 10 and 20 wt %.

Alternatively, the flammable macromolecular material (a) is a thermosetting polymer, such as an epoxy resin, an unsaturated polyester, a polyurethane and/or a rubber.

DESCRIPTION OF THE EMBODIMENTS

Described herein is a halogenated aryl ether oligomer formed by halogenation, particularly bromination, of an aryl ether oligomer and use of the halogenated oligomer as a flame retardant for flammable macromolecular polymers. Suitable macromolecular polymers include thermoplastic polymers, such as polystyrene, poly (acrylonitrile butadiene styrene), polycarbonates, polyolefins, polyesters and polyamides, and thermosetting polymers, such as epoxy resins, unsaturated polyesters, polyurethanes and rubbers.

The term "oligomer" is used herein to mean a compound formed by oligomerization of one or more monomers so as to have repeating units derived from said monomer(s) irrespective of the number of said repeating units. Because the aryl ether precursor used to the produce the present flame retardant is produced by an oligomerization process, the precursor and the halogenated product will generally have a distribution of molecular weight. In particular, the oligomer generally has an average of least 3 aryl and typically at least 5 aryl rings, with the average molecular weight of the halogenated oligomer being up to 1,000,000 Daltons.

Typically, the present halogenated aryl ether oligomer comprises the following repeating monomeric units:

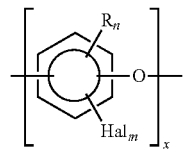

wherein R is hydrogen or alkyl, especially $C_1$ to $C_4$ alkyl, Hal is halogen, m is at least 1, n is 0 to 3 and x is at least 2, such as 3 to 100,000, for example 5 to 20. The halogen can be fluorine, chlorine, bromine and/or iodine, especially bromine. Generally, the halogenated aryl ether oligomer also comprises end groups each independently comprising an alkyl, alkoxy, aryl, aryloxy, hydrogen, halide or hydroxyl group.

In one embodiment, the halogenated aryl ether oligomer flame retardant has the following formula:

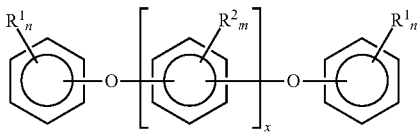

wherein each $R^1$ is independently selected from hydrogen, hydroxy, halogen and alkyl, wherein each $R^2$ is independently selected from hydrogen, hydroxy, halogen and alkyl, provided at least one $R^2$ is halogen, normally bromine, n is 5, m is 4, and x is from 1 to 100,000, for example from 3 to 20.

Generally, the halogen content of the present halogenated aryl ether oligomer is in the range of about 50 to about 83 wt %, such as in the range of about 65 to about 80 wt % of the oligomer.

In another embodiment, the flame retardant used herein comprises a halogenated aryl ether having the following formula:

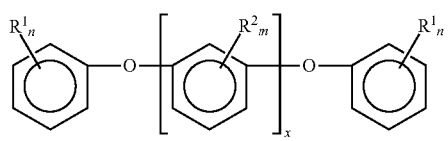

wherein each $R^1$ is independently selected from hydrogen, hydroxy, halogen and alkyl, wherein each $R^2$ is independently selected from hydrogen, hydroxy, halogen and alkyl, provided at least one $R^2$ and normally at least one $R^1$ is halogen, normally bromine, n is 5, m is 4, and x is from 1 to 10, for example from 2 to 6. In the case of this embodiment, the halogenated aryl ether may have an oligomeric distribution or may be a discrete compound.

The present flame retardant is produced by halogenation, normally bromination, of a polyaryl ether precursor, which in torn can be made by oligomerization of a hydroxyhaloaryl material, such as bromophenol, or reaction of a dihalo aryl material, such as dibromobenzene, with a dihydroxyaryl material, such as resorcinol, using an ether synthesis, such as the Ullmann ether synthesis. In this process, the reagents are heated under reflux, typically at about 125° C. to about 200° C., in a polar organic solvent, such as N,N-dimethylformamide or benzophenone, in the presence of a strong base and a copper-containing catalyst. A representative disclosure of the Ullmann ether synthesis is given by Laskoski et al. in "Oligomeric Cyanate Ester Resins: Application of a Modified Ullmann Synthesis in the Preparation of Thermosetting Polymers", *Journal of Polymer Science: Part A: polymer Chemistry*, Vol. 44, (2006), pages 4559-4565.

Bromination of the resultant polyaryl ether is readily achieved by the reaction of the polyaryl ether with bromine in the presence of a Lewis acid catalyst, such as aluminum chloride. Depending on the amount of bromine desired to be introduced into the aryl ether oligomer, the weight ratio of bromine to oligomer employed in the bromination reaction is typically between about 1:1 and about 100:1, such as between about 3:1 and about 20:1. The final brominated aryl ether oligomer is generally arranged to have at least one, and typically between 2 and 4 bromine atoms per aryl ether repeating unit of the oligomer.

Alternatively, bromine chloride may be used as the brominating agent to generate the desired product in similar fashion. In this case, a small amount of organically-bound chlorine would also be present, but would not detract from the properties of the final flame retardant.

The resultant halogenated aryl ether oligomer can be used as a flame retardant for many different polymer resin systems because of its high thermal stability and also because of its relatively high halogen content compared with existing polymeric flame retardant products, such as brominated polystyrenes. Generally, the halogenated aryl ether oligomer is employed as a flame retardant with thermoplastic polymers, such as polystyrene, high-impact polystyrene (HIPS), poly (acrylonitrile butadiene styrene) (ABS), polycarbonates (PC), PC-ABS blends, polyolefins, polyesters and/or polyamides. With polymers, the level of the halogenated oligomer in the polymer formulation required to give a V-0 classification when subjected to the flammability test protocol from Underwriters Laboratories is generally within the following ranges:

| Polymer | Useful | Preferred |
|---|---|---|
| Polystyrene | 5 to 25 wt % | 10 to 20 wt % |
| Polypropylene | 20 to 50 wt % | 25 to 40 wt % |
| Polyethylene | 5 to 35 wt % | 20 to 30 wt % |
| Polyamide | 5 to 25 wt % | 10 to 20 wt % |
| Polyester | 5 to 25 wt % | 10 to 20 wt %. |

The present halogenated aryl ether oligomer can also be used with thermosetting polymers, such as an epoxy resins, unsaturated polyesters, polyurethanes and/or rubbers. Where the base polymer is a thermosetting polymer, a suitable flammability-reducing amount of the oligomer is between about 5 wt % and about 35 wt %, such as between about 10 wt % and about 25 wt %.

Typical applications for polymer formulations containing the present halogenated aryl ether oligomer as a flame retardant include automotive molded components, adhesives and sealants, fabric back coatings, electrical wire and cable jacketing, and electrical and electronic housings, components and connectors. In the area of building and construction, typical uses for the present flame retardant include self extinguishing polyfilms, wire jacketing for wire and cable, backcoating in carpeting and fabric including wall treatments, wood and other natural fiber-filled structural components, roofing materials including roofing membranes, roofing composite materials, and adhesives used to in construction of composite materials. In general consumer products the present flame retardant can be used in formulation of appliance parts, housings and components for both attended and unattended appliances where flammability requirements demand.

The invention will now be more particularly described with reference to the following non-limiting Examples.

EXAMPLES 1 to 7

Bromination Of Aryl Ether Resin

Bromine (3176 g, 19.87 mol) was added to a solution of 500 g of aryl ether resin (Santovac OS-124) in 1 L of dichloroethane containing 6.5 g of $AlCl_3$ catalyst. The Santovac OS-124 is an aryl ether resin containing five aryl rings connected in the meta position and was used to simulate an oligomeric material. After work-up, the brominated resin was isolated to give 2013.6 g of a pale cream powder as the product. The material analyzed to contain 75.7% bromine and the TGA analysis showed a 5% wt loss at 420° C. Differential Scanning Calorimetry (DSC) analysis showed a glass transition (Tg) at 154° C.

Several additional materials were prepared in similar fashion to give brominated aryl ether materials containing different levels of bromine or different ring connectivities, as shown in Table 1. The bromination level was found to influence the observed glass transition temperatures and melt-ranges of the products.

TABLE 1

| Example | Oligomer Type[a] | % Bromine | Tg, ° C. (DSC) | Visual Melt Range, ° C. |
|---|---|---|---|---|
| 1 | 5-meta | 75.7 | 154 | 177-211 |
| 2 | 5-meta | 65.5 | 77.0 | 87-109 |
| 3 | 5-meta | 74.7 | 150.8 | 160-183 |
| 4 | 5-meta | 80.0 | 192.1 | 204-221 |
| 5 | 6-meta | 74.8 | 160.5 | 184-198 |
| 6 | 3-para | 72.6 | 85.3 | 185-241 |
| 7 | 4-para | 70.8 | 130.5 | 168-196 |

[a]Nomenclature: 5-meta means 5 aryl rings connected by all meta linkages.

EXAMPLE 8

Polyarylether Synthesis From Resorcinol And 1,4-Dibromobenzene

A reaction flask was charged with resorcinol (15.0 g, 0.137 mole), 1,4-dibromobenzene (32.3 g, 0.137 mole), N,N-dimethylformamide (205 g, 2.58 mole), toluene (20 g, 0.22 mole), and a 50% solution of KOH, which was made by dissolving 90% KOH (17.05 g, 0.274 mole) in DI water. The amount of base typically ranges from 1.8 to 2.2 mole per mole of resorcinol. The reaction mixture was heated to reflux to azeotropically remove the water. After the theoretical amount of water was removed, most of the toluene was stripped from the reaction flask to a final pot temperature of 148-150° C. Then, the reaction was cooled to ~120° C. and CuI (0.52 g, 0.00274 mole) and 1,10-phenanthroline (0.74 g, 0.0041 mole) were added simultaneously under a heavy nitrogen stream. The reaction flask was blanketed under nitrogen and the mass heated to reflux (~150-155° C.) for 24 hour and then cooled for workup. The worked up involved acidification of the mixture to a pH of 2-3 with 2% HCl followed by extraction with methylene chloride or chloroform. The organic phase was stripped to give a viscous resin product residue with an isolated yield=92%. GPC analysis of the product gave a molecular weight (Mw) of 605 and polydispersity (Pd) of 1.97.

GPC analysis of various reaction products produced by this approach gave an Mw ranging from 600 to 3100.

EXAMPLE 9

Polyarylether Synthesis From 3-Bromophenol In Dmf/Toluene

3-Bromophenol (100 g, 0.58 mole), toluene (700 g), and 50% KOH (72 g, 0.58 mole) were added to a standard reaction flask. The contents were heated to reflux and the water was removed azeotropically. An additional 540 grams of toluene was Stripped from the reaction flask. The contents of the flask were cooled to 100° C. and DMF (467 grams), CuI (0.22 g, 0.0012 mole), and 1,10-phenanthroline (0.31 g, 0.0017 mole) were added. The contents of the flask were heated back to reflux. Additional toluene was stripped until the temperature reached 140° C. and bromobenzene (4.55 grams, 0.029 mole) was then added. After the reaction was complete, the product was worked up to give a viscous amber colored resin in 91.1% yield. This product polymer had a molecular weight by GPC analysis of 2270 Mw.

EXAMPLE 10

Polyarylether Synthesis from 4-Bromophenol with Benzophenone as Solvent

A reaction flask was charged with 4-bromophenol (232.5 g, 1.34 mole), benzophenone (1435 g, 8.04 mole), and toluene (900 g, 1.34 mole). The flask was purged with $N_2$ and was heated to <100° C. to dissolve the benzophenone. A 50% solution of KOH was prepared by dissolving 90% KOH (83.5 g, 1.34 mole) in 83.5 g DI water. The KOH solution was added to the flask over a period of 5 minutes and contents of the flask were heated to reflux. The water was removed azeotropically and the toluene was distilled out. Bromobenzene (10.5 g, 0.07 mole) was added along with a solution of CuCl (1.33 g, 0.0134 mole) dissolved in pyridine (90 g, 0.134 mole). The reaction was held at 204° C. for 5 hours. The reaction was cooled and worked up to give 165.7 g (65% yield) of light tan solids. Analysis by GPC (THF solvent system) gave Mw=1790 and Pd=1.70 (not all the material was soluble).

Due to lack of complete solubility in the solvent used for GPC determinations, a secondary analysis of molecular weight was conducted based on DSC. A series of model compounds of para aryl ethers containing 3, 4, and 5 rings were analyzed by DSC and found to have melting points that fit to a straight line equation. Included in this analysis was diphenyl ether, which fit the line as expected. The mp data is as follows for the para model series (2 ring through 5 ring): 26, 75.6, 108.2, 147.4° C. This line was used to estimate the number of aryl groups on the polymer that was made, which would only be a crude estimation of molecular weight. By this approach, the number of aryl rings was predicted to be 8.

EXAMPLES 11 And 12

Bromination of Aryl Ethers from 4-Bromophenol Polymerization

A reaction flask was charged with 100.0 g of the polyphenyl ether produced in Example 10, 600 ml of chloroform and 10.2 g of aluminum chloride. The resulting slurry was heated to reflux (60° C.) and 1202.41 g of dry bromine was added over 6 hours while maintaining reflux. The reaction mass was held at reflux temperature for 2 hours and worked up to give a solid precipitate. The resulting polymeric product (223.2 g), was a tan solid, with the following analysis: 68.8% OBr, melt range 230-313° C. The properties of the product are shown in Table 2.

The above bromination method was repeated to give, a brominated oligomeric aryl ether material containing a different level of bromine, as shown in Table 2.

EXAMPLES 13 And 14

Bromination of Aryl Ethers from 3-BrPhOH Polymerization

A large-scale reaction from Example 9 was conducted by using a 0.20 mol ratio of bromobenzene endcap to 3-bromophenol, generating a material that analyzed to have a slightly lower molecular weight by GPC of 700 Mw. A reaction flask was charged with 108.2 g of this polyphenyl ether, 1000 ml of chloroform and 10.8 g of aluminum chloride. The resulting slurry was heated to reflux (60° C.) and 1044.1 g of dry bromine was added over 8 hours while maintaining reflux. The reaction mass was held at reflux temperature for 1 hour and worked up to give a solid precipitate. The resulting polymeric product (319.9 g), was a brown solid, with the following analysis: 70.2% OBr, melt range 141-161° C., DSC showed a glass transition (Tg) at 117° C. The properties of the product are shown in Table 2.

The above bromination method was repeated to give a brominated oligomeric aryl ether material containing a different level of bromine, as shown in Table 2.

By comparing the results in Table 2, it will be seen that by varying the regiochemistry of the oligomer (meta vs para), oligomers with different glass transition temperatures and visual melt-ranges were produced. It is also possible to prepare a mixed oligomer having a blend of meta and para connectivities by using the appropriate reagents and ratios during the reaction.

TABLE 2

| Example | Oligomer Type | GPC (Mw)[a] | % Bromine | Tg, ° C. (DSC) | Melt Range, ° C. |
|---|---|---|---|---|---|
| 11 | Para | 1790 | 68.8 | >240 | 230-313 |
| 12 | Para | 1700 | 58.7 | >240 | 216-293 |
| 13 | Meta | 700 | 70.2 | 117 | 141-161 |
| 14 | Meta | 1020 | 64.1 | 123 | 141-164 |

[a]GPC analysis was conducted on the oligomer prior to bromination. The para samples were only partially soluble.

EXAMPLE 15

Compounding of Brominated Aryl Ether Oligomers in HIPS Resin

The brominated aryl ether oligomers prepared in Examples 1 to 4 (Table 1) were separately compounded with HIPS (high impact polystyrene) resin formulations containing antimony oxide (ATO) synergist using a twin-screw extruder with barrel temperatures of 200-220° C. For comparison, similar formulations were prepared using deca and deca-DPE as the flame retardants. The resultant formulations were injection-molded into test bars and evaluated as shown in Table 3. The mechanical property and MFI tests were conducted according to the normal ASTM methods. The glass-transition temperatures of the brominated aryl ether oligomers were all below the compounding temperatures of the resin, indicating that the oligomers would be melt-blendable in this system. Note that deca and deca-DPE are not melt-blendable and act as filler type materials. This data shows correlation between melt flow index (MFI) of the compounded material and the Tg of the FR that was used, which is somewhat expected. The data also shows that the Vicat softening point is not really influenced by the flame retardant type that was used, except for the lower Tg sample, which is also reasonable:

TABLE 3

| | Formulation No | | | | | |
|---|---|---|---|---|---|---|
| | 15-A | 15-B | 15-C | 15-D | 15-E | 15-F |
| FR | Deca | Deca-DPE "83" | Example 1 | Example 2 | Example 3 | Example 4 |
| FR, % Br | 83 | | 75.7 | 65.5 | 74.7 | 80.0 |
| FR Tg, °C. | NA | NA | 154 | 77 | 151 | 192 |
| Formulation | | | | | | |
| Polystyrene Resin | 77.3 | 77.3 | 75.95 | 73.6 | 75.7 | 76.8 |
| FR | 14.0 | 14.0 | 15.35 | 17.7 | 15.6 | 14.5 |
| ATO | 3.5 | 3.5 | 3.5 | 3.5 | 3.5 | 3.5 |
| Anox PP-18 | 0.2 | 0.2 | 0.2 | 0.2 | 0.2 | 0.2 |
| Kraton D1101 | 5.0 | 5.0 | 5.0 | 5.0 | 5.0 | 5.0 |
| Test Results | | | | | | |
| MFI (g/10 min) | 9.7 | 7.7 | 9.4 | 19.2 | 9.7 | 8.9 |
| Vicat, °C. | 96.2 | 97.6 | 98.7 | 92.9 | 99.2 | 100.4 |
| Izod Notched Impact Strength (ft-lb/in) | 2.1 | 2.05 | 3.2 | 2.5 | 2.7 | 2.5 |
| UL-94 (1/16") | V-0 | V-0 | V-0 | V-0 | V-0 | V-0 |

The surprising result lies in the impact strength data. When comparing the formulations with the two control samples, the aryl ether oligomer systems show an actual increase in impact strength. A wide range of Tg can be used while still obtaining good mechanical properties. This result could be due to an improvement in resin-FR compatibility, domain size of the FR material in the test bars, or some other factor. These data indicate that the properties of the final formulation can be optimized by adjusting the FR oligomer glass transition temperature. This would not be possible with brominated small molecules, as they typically are high-melting solids.

EXAMPLE 16

Compounding of Brominated Aryl Ether Oligomers in HIPS Resin

The brominated aryl ether oligomers prepared in Example 12 (Table 2) were separately compounded with HIPS (high impact polystyrene) resin formulations containing antimony oxide synergist using a twin-screw extruder with barrel temperatures of 200-220° C. These formulations were injection-molded into test bars and evaluated as shown in Table 4. Two of these FR oligomer materials have Tg values below the compounding temperatures and two have Tg values somewhere above that temperature. The latter two would, therefore, not be melt-blendable and the resulting MFI values are expectedly lower. Interestingly, these samples based on the para aryl ether gave reduced impact strength properties and those based on the meta aryl ethers gave good impact strength values. This could be a reflection of different compatibilities between the FR types and the resin, or related to how the materials coalescence in formulation upon cooling, or some other factor.

TABLE 4

| | Formulation No. | | | | |
|---|---|---|---|---|---|
| | 16-A | 16-B | 16-C | 16-D | 16-E |
| FR | Deca | Example 12 | Example 11 | Example 13 | Example 14 |
| FR, % Br | 83 | 58.7 | 68.8 | 70.2 | 64.1 |
| FR Tg, °C. | NA | >240 | >240 | 117 | 123 |
| Formulation | | | | | |
| Polystyrene Resin | 77.3 | 71.5 | 74.4 | 74.55 | 73.2 |
| FR | 14.0 | 19.8 | 16.9 | 16.55 | 18.1 |
| ATO | 3.5 | 3.5 | 3.5 | 3.5 | 3.5 |
| Anox PP-18 | 0.2 | 0.2 | 0.2 | 0.2 | 0.2 |
| Kraton D1101 | 5.0 | 5.0 | 5.0 | 5.0 | 5.0 |
| Test Results | | | | | |
| MFI (g/10 min) | 9.7 | 5.6 | 5.7 | 12.1 | 11.7 |
| Vicat, °C. | 96.2 | 99.6 | 98.2 | 97.8 | 98.1 |
| Izod Notched Impact Strength (ft-lb/in) | 2.1 | 1.2 | 0.7 | 2.2 | 1.9 |
| UL-94 (1/16") | V-0 | V-1 | V-1 | V-0 | V-0 |

EXAMPLE 17

Compounding of Brominated Aryl Ether Oligomers in HIPS Resin

Since the impact strength for some of the formulations in Examples 15 and 16 was actually higher than the standard deca type control runs, a study was conducted in which the flame retardant of Example 1 was employed and impact modifier (Kraton D1101) was reduced, as shown in Table 5. This study shows that the impact modifier can indeed be reduced or potentially eliminated from a HIPS formulation and still be as good as (or close to) the deca control formulation, and that there is room for further formulation optimization of properties.

TABLE 5

|  | Formulation No | | | |
|---|---|---|---|---|
|  | 17-A | 17-B | 17-C | 17-D |
| FR | Deca | Example 1 | Example 1 | Example 1 |
| FR, % Br | 83 | 73.1 | 73.1 | 73.1 |
| FR Tg, ° C. | NA | 148 | 148 | 148 |
| Formulation |  |  |  |  |
| Polystyrene Resin | 77.3 | 75.9 | 78.4 | 80.9 |
| FR | 14.0 | 15.4 | 15.4 | 15.4 |
| ATO | 3.5 | 3.5 | 3.5 | 3.5 |
| Anox PP-18 | 0.2 | 0.2 | 0.2 | 0.2 |
| Kraton D1101 | 5.0 | 5.0 | 2.5 | 0 |
| Test Results |  |  |  |  |
| MFI (g/10 min) | 9.7 | 12.5 | 14.3 | 15.5 |
| Vicat, ° C. | 96.2 | 99.3 | 99.1 | 98.6 |
| Izod Notched Impact Strength (ft-lb/in) | 2.1 | 2.6 | 2.2 | 1.8 |
| UL-94 (1/16") | V-0 | V-0 | V-0 | V-0 |

EXAMPLE 18

Compounding of Brominated Aryl Ether Oligomers in Polyamide

The brominated aryl ether oligomers shown in Table 1 were compounded with glass-reinforced PA66 resin containing antimony oxide synergists. These formulations were molded into test bars and evaluated as shown in Table 6. This set of data compares the oligomeric aryl ether flame retardants with a commercially available brominated polystyrene (Saytex™ HP-3010). The results show that the aryl ether is more efficient, showing a V-0 at 13.3% loading and a strong V-0 at 16% loading, as compared with the 20% loading for the HP-3010 material. The data also shows a slight improvement in mechanical properties with tensile strength being about the same, but tensile elongation showing about a 20% improvement.

TABLE 6

|  | Formulation No. | | | | |
|---|---|---|---|---|---|
|  | 18-A- | 18-B | 18-C | 18-D | 18-E |
| FR | None | HP-3010 | Ex. 1 | Ex. 1 | Ex. 2[a] |
| FR, % Br | — | 68 | 75.7 | 75.7 | 63.0 |
| Formulation |  |  |  |  |  |
| PA66 Resin | 70 | 41.2 | 50.65 | 47.15 | 42.65 |
| Glass Fiber | 30 | 30 | 30 | 30 | 30 |
| FR |  | 20 | 13.5 | 16.0 | 19.8 |
| ATO |  | 8.45 | 5.5 | 6.5 | 1.2 |
| Magnesium stearate |  | 0.35 | 0.35 | 0.35 | 0.35 |
| Test Results |  |  |  |  |  |
| Tensile Strength, Kpsi | 26.9 | 21.3 | 21.4 | 21.0 | NA |
| Tensile Elongation, % | 3.91 | 1.89 | 2.39 | 2.22 | NA |
| Sprial flow, in. | 23.8 | 30.4 | 26.3 | 28.2 | NA |
| Viscosity, Pa-s @ 1000 s$^{-1}$ | 168.8 | 103.2 | 106.0 | 100.8 | NA |
| UL-94 total burn time (5 bars), s | NA | 5 | 36 | 2 | 14 |
| UL-94 (1/32") | FAIL | V-0 | V-0 | V-0 | V-0 |

[a]A scale-up of Example 2; Analysis: m.p. 96-113° C., % Bromine = 63.0%

In order to determine if the improved flame retardant efficiency is a result of the higher bromine content, or is related to the structure of the oligomer, a lower bromine content sample was also tested. The results showed that at the same load level as the 68% bromine content brominated polystyrene material (i.e. lower overall bromine content), the formulation was a strong V-0. This indicated that the structure is contributing to the improved FR efficiency.

EXAMPLE 19

Compounding of Different Flame Retardants in Polypropylene

The brominated aryl ether oligomer of Example 3 was compounded with Profax 6323 polypropylene homopolymer containing an antimony oxide synergist and, for comparison, similar formulations were prepared using deca and deca-DPE as the flame retardant. The formulations were compounded using a twin-screw extruder with barrel temperature of about 200° C., injection-molded into test bars and evaluated as shown in Table 7.

TABLE 7

|  | Formulation No | | | |
|---|---|---|---|---|
|  | 19-A | 19-B | 19-C | 19-D |
| Profax 6323 PP homopolymer (%) | 100 | 59 | 55.8 | 59 |
| Deca (%) |  | 35 |  |  |
| Bromo(polyaryl ether) Ex. 3 (%) |  |  | 38.2 |  |
| Deca-BDE (%) |  |  |  | 35 |
| ATO (%) |  | 6 | 6 | 6 |
| UL-94 Rating |  | V-0 | V-0 | V-0 |
| MFI (g/10 min) | 12.4 | 11.2 | 47.4 | 12.1 |
| HDT (° C.), 264 psi | 84 | 112 | 120 | 117 |

These results show a significant increase in the melt flow property with a slightly higher increase in Heat Deflection Temperature (HDT) for the oligomeric FR product as compared with the deca and deca-DPE control samples.

The formulations were also subjected to a bloom test by placing the UL test bars in an oven at 80° C. The bars were pulled out of the oven at 24 hours and after 1 week and wiped with a black cloth to pick up bloom if present. Bloom is a migration of the flame retardant or other additive to the surface and usually shows as a visible dust on the test cloth. There was no bloom present on the oligomeric FR formulation bars, whereas the other two flame retardant formulations showed bloom.

EXAMPLE 20

Compounding of Different Flame Retardants in Low Density Polyethylene

The brominated aryl ether oligomer of Example 3 was compounded with Petrothene NA820000 NT low density polyethylene and, for comparison, similar formulations were prepared using deca and deca-DPE as the flame retardant. The formulations were compounded using a twin-screw extruder with barrel temperature of about 190° C., injection-molded into test bars and evaluated as shown in Table 8.

TABLE 8

|  | Formulation No | | | |
| --- | --- | --- | --- | --- |
|  | 20-A | 20-B | 20-C | 20-D |
| Resin | Petrothene NA820000 NT LDPE | | | |
| FR | None | Deca | Ex. 3 | Deca-BDE |
| FR % |  | 24 | 26.2 | 24 |
| MFI (g/10 min) | 1.33 | 1.54 | 2.38 | 1.35 |
| HDT (° C.), 264 psi | 39.6 | 42.1 | 66.9 | 42.3 |
| Flexural Properties | | | | |
| Strength (ksi) | 1.2 | 1.5 | 2.3 | 1.5 |
| Modulus (ksi) | 19.1 | 27.1 | 56.5 | 27 |
| UL-94 Rating | FAIL | V-0 | V-0 | V-0 |

For this resin system, the MFI and HDT properties both increased when the oligomeric flame retardant was used as compared the brominated control samples. Additionally, it was found that the flexural properties also increased. A bloom test was conducted as described in the pervious example and the oligomeric FR formulation showed just a faint trace of bloom, whereas the deca formulation showed a large amount of bloom on the test cloth.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A flame retardant polymer composition comprising
   (a) a thermoplastic polymer and
   (b) a halogenated aryl ether flame retardant of formula:

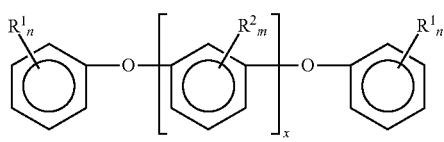

wherein
each $R^1$ is independently selected from hydrogen, halogen and alkyl;
each $R^2$ is independently selected from hydrogen, halogen and alkyl;
n is 5, m is 4, x is from 2 to 6
provided at least one $R^2$ and at least one $R^1$ is halogen,
and wherein the halogen content of the halogenated aryl ether flame retardant is in the range of about 50 to about 83 wt %.

2. The flame retardant polymer composition of claim 1 wherein each $R^1$ and each $R^2$ is independently selected from hydrogen and halogen.

3. The flame retardant composition of claim 2 wherein the halogen content of the halogenated aryl ether flame retardant is in the range of about 65 to about 80 wt %.

4. The flame retardant composition of claim 1 wherein the halogen content of the halogenated aryl ether flame retardant is in the range of about 65 to about 80 wt %.

5. The flame retardant polymer composition of claim 2 wherein each $R^1$ and each $R^2$ is independently selected from hydrogen and bromine.

6. The flame retardant polymer composition of claim 1 wherein each $R^1$ and each $R^2$ is independently selected from hydrogen and bromine.

7. The flame retardant polymer composition of claim 1 wherein the halogenated aryl ether flame retardant comprises more than one compound of formula:

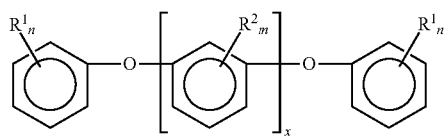

wherein
each $R^1$ is independently selected from hydrogen, halogen and alkyl;
each $R^2$ is independently selected from hydrogen, halogen and alkyl;
n is 5, m is 4, x is from 2 to 6
provided at least one $R^2$ and at least one $R^1$ is halogen,
and wherein the halogen content of the halogenated aryl ether flame retardant is in the range of about 50 to about 83 wt %.

8. The flame retardant polymer composition of claim 7 wherein the halogenated aryl ether flame retardant comprises a compound wherein x is 3.

9. The flame retardant polymer composition of claim 1 wherein the halogenated aryl ether flame retardant comprises an oligomeric distribution of compounds of formula:

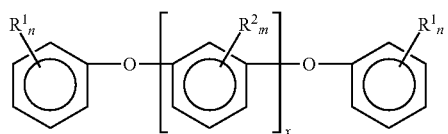

wherein
each $R^1$ is independently selected from hydrogen, halogen and alkyl;
each $R^2$ is independently selected from hydrogen, halogen and alkyl;
n is 5, m is 4, x is from 2 to 6
provided at least one $R^2$ and at least one $R^1$ is halogen,
and wherein the halogen content of the halogenated aryl ether flame retardant is in the range of about 50 to about 83 wt %.

10. The flame retardant polymer composition of claim 9 wherein the halogenated aryl ether flame retardant comprises an oligomeric distribution containing a compound wherein x is 3.

* * * * *